United States Patent [19]

Guth et al.

[11] 4,443,362

[45] Apr. 17, 1984

[54] DETERGENT COMPOUNDS AND COMPOSITIONS

[75] Inventors: Jacob J. Guth, Upper Black Eddy, Pa.; Robert J. Verdicchio, Succasunna, N.J.

[73] Assignee: Johnson & Johnson Baby Products Company, New Brunswick, N.J.

[21] Appl. No.: 278,284

[22] Filed: Jun. 29, 1981

[51] Int. Cl.$^3$ .................... C11D 1/88; C07C 101/04; C07C 101/20
[52] U.S. Cl. .................... 252/545; 252/546; 252/DIG. 13; 252/DIG. 14; 260/501.11; 260/501.12; 424/70
[58] Field of Search .................... 260/501.11, 501.12; 424/70; 562/587, 571; 252/545, 546, 547, DIG. 13, DIG. 14

[56] References Cited

U.S. PATENT DOCUMENTS

| | | | |
|---|---|---|---|
| 2,097,864 | 11/1937 | Platz et al. | 562/571 X |
| 2,781,390 | 2/1957 | Mannheimer | 260/501.12 X |
| 2,876,259 | 3/1959 | Nordgren | 562/571 X |
| 3,198,822 | 8/1965 | Mannheimer | 260/501.12 X |
| 3,452,066 | 6/1969 | Mannheimer | 260/501.12 X |
| 4,098,818 | 7/1978 | Krummel et al. | 562/587 |
| 4,107,096 | 8/1978 | McEntire et al. | 260/501.11 X |

OTHER PUBLICATIONS

Schwartz et al, Surface Active Agents, vol. I (1949) 25–27 & 218–228.

*Primary Examiner*—Bernard Helfin
*Attorney, Agent, or Firm*—Steven P. Berman

[57] ABSTRACT

Novel amphoteric-alkoxylated carboxylate complexes are described as well as detergent compositions containing said complexes.

10 Claims, No Drawings

DETERGENT COMPOUNDS AND COMPOSITIONS

BACKGROUND OF THE INVENTION

The present invention relates to amphoteric-alkoxylated carboxylic acid complexes. More specifically, the invention relates to amphoteric-alkoxylated carboxylate complexes which exhibit desirable foam properties and low ocular irritancy. The invention further relates to detergent compositions containing the novel amphoteric-alkoxylated carboxylate complexes in combination with other surfactants and/or detergent components.

Nonirritating detergent compositions have been known in the art and have been in use for some time. U.S. Pat. Nos. 3,299,069 and 3,055,836 are merely two representative examples of such prior art nonirritating detergent compositions. Likewise, amphoteric compounds have been well known in the art and have been disclosed in use with various other detergent compounds. U.S. Pat. No. 2,528,380, discloses a ring structured amphoteric compound with a fatty acid attached to the ring nitrogen. Copending U.S. patent application Ser. No. 241,862 filed Mar. 9, 1981, relates to various amphoteric-fatty acid complexes. None of the teachings in the prior art disclose the amphoteric-alkoxylated carboxylate complexes of the present invention nor the advantages provided by same.

It is an object of the present invention to provide novel detergent compounds.

It is another object of the present invention to provide novel detergent compounds which exhibit good foam properties and low ocular irritancy.

It is a further object of the present invention to provide detergent compositions which exhibit good foam properties and low ocular irritancy.

These and other objects of the present invention will become apparent to one skilled in the art from the detailed description given hereinafter.

SUMMARY OF THE INVENTION

This invention encompasses non-zwitterionic, amphoteric-alkoxylated carboxylate complexes of the formula

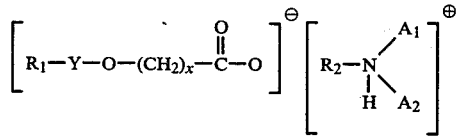

wherein $R_1$, $R_2$, $A_1$, $A_2$, x and Y are as defined below.

DETAILED DESCRIPTION OF THE INVENTION

The present invention relates to novel non-zwitterionic, amphoteric-alkoxylated carboxylate complexes of the formula

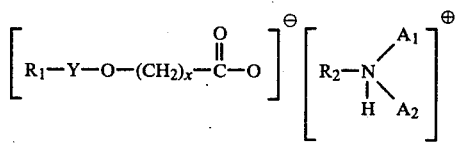

wherein $R_1$ is alkyl or substituted alkyl containing from about 6 to 18 carbon atoms and mixtures thereof;

$R_2$ is alkyl containing from about 8 to 18 carbon atoms and mixtures thereof of alkyl amido of the formula

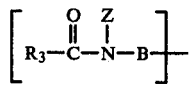

wherein $R_3$ is alkyl containing from about 7 to 17 carbon atoms,

Z is H or lower alkyl containing from 1 to 4 carbon atoms; and

B is lower alkyl containing from 1 to 4 carbon atoms; $A_1$ and $A_2$ are the same or different and are selected from the group of anionic salt moieties consisting of the following:

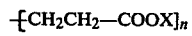

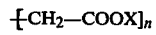

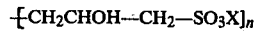

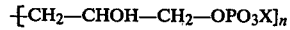

wherein X is a water-soluble cation such as $Na^+$, $K^+$ $Ca^{++}$, $Mg^{++}$ and the like and n is an integer of 1 or 2 with the proviso that if only one of $A_1$ and $A_2$ are selected from the anionic salt moieties above the other can be lower alkyl or lower hydroxyalkyl containing from 1 to 4 carbon atoms;

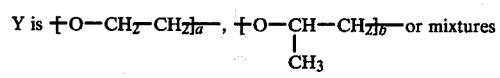

thereof wherein a and b are the same or different and are integers of from 1 to 100; and x is an integer of from 1 to 3.

The non-zwitterionic, amphoteric compounds which are useful in the complexes of the present invention are of the formula:

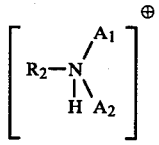

wherein $R_2$, $A_1$ and $A_2$ are as defined above.

These compounds can be prepared in accordance with the teachings of the art, see for example, U.S. Pat. No. 2,970,160, which is incorporated herein by reference.

The alkoxylated carboxylate compounds which are useful in the complexes of the present invention are of the formula:

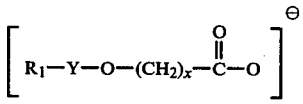

wherein $R_1$, Y and x are as defined above. These compounds are readily available commercially from Sandoz Chemical Company under the tradename Sandopans as Specific examples of the novel amphoteric-alkoxylated carboxylate complexes of the present invention include:

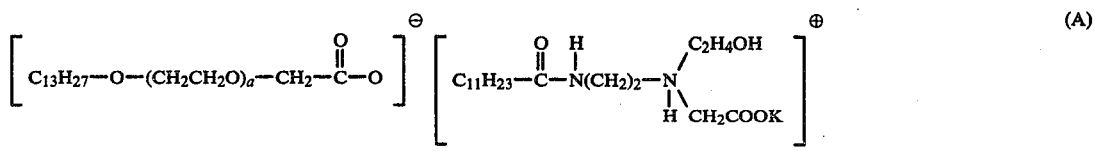
(A)

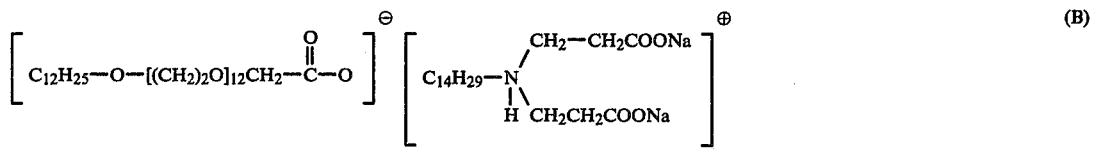
(B)

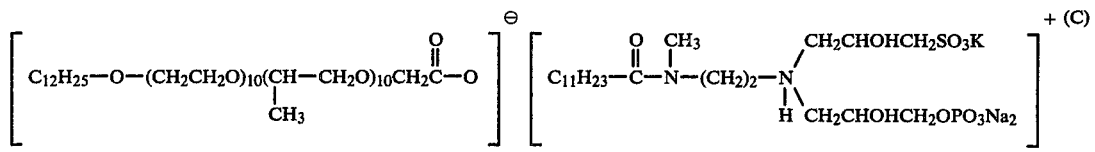
(C)

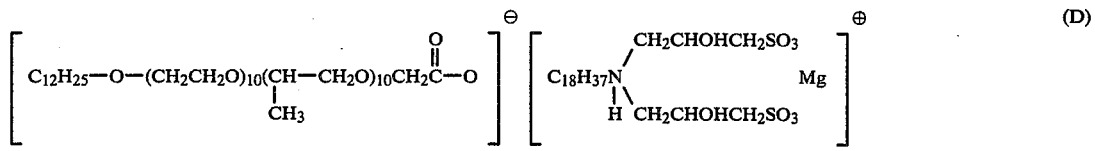
(D)

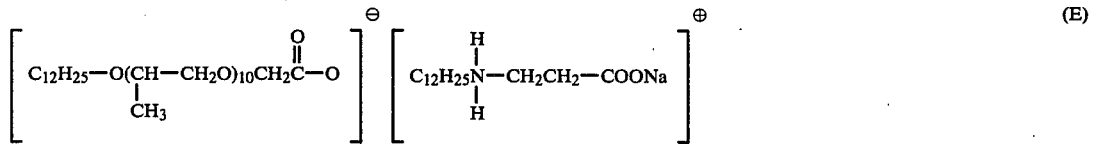
(E)

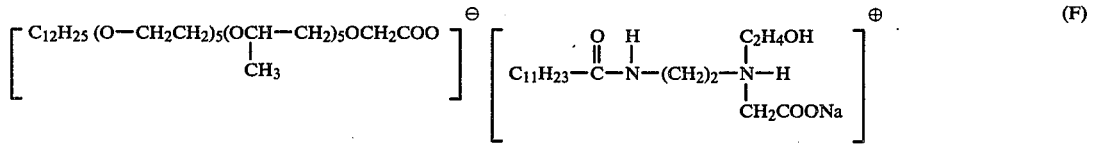
(F)

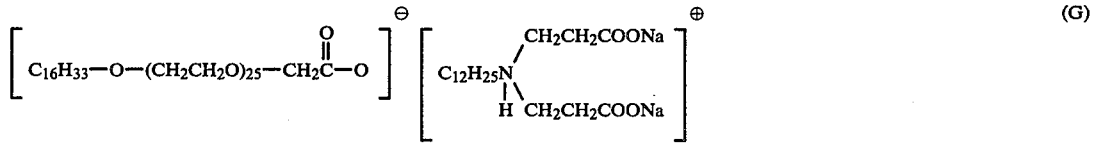
(G)

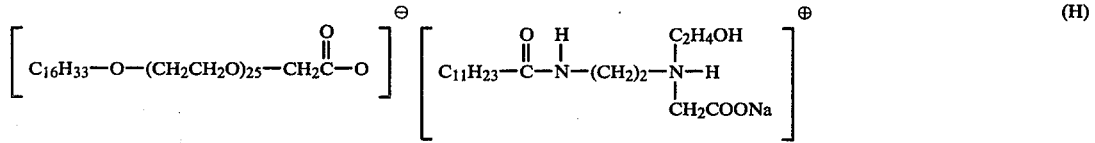
(H)

well as from various other commercial suppliers.

The amphoteric-alkoxylated carboxylate complexes of the present invention can be prepared by admixing a suitable non-zwitterionic amphoteric and a suitable alkoxylated carboxylate, utilizing heat, if necessary, to facilitate the blending and adding water, if needed. The ratio of alkoxylated carboxylate to amphoteric can be in the range of about 0.5:1 to 1.5:1, preferably about 1:1. The pH of the resulting complex should be within the range of 6.5–8.5, preferably within the range of 7.0–7.5, to minimize potential irritation problems.

The amphoteric-alkoxylated carboxylate complexes of the present invention exhibit excellent surfactant properties. In particular, these complexes exhibit good foam and cleansing properties and low ocular irritancy.

These complexes can be utilized in detergent compositions either alone or in combination with other surfactants in a range of from about 1.0 to 50.0% by weight of the total compositions.

The amphoteric surfactants which may be used in the present invention include betaines, sultaines, phosphobetaines, phosphitaines, n-alkylamino propionates, n-alkylimino dipropionates and imidazolines. The betaine and sultaine surfactants useful in this invention are described in U.S. Pat. No. 3,950,417 issued Apr. 13, 1976, which is incorporated herein by reference. The phosphobetaines and phosphitaines useful in this invention are described in U.S. Pat. No. 4,215,064 and copending application Ser. No. 965,462 filed Nov. 30, 1978 and now U.S. Pat. No. 4,261,911, both of which are incorporated herein by reference. The n-alkylamino propionates and n-alkylimino dipropionates are sold under the tradename Deriphats by General Mills. The imidazolines which are useful in the compositions of this invention are described in U.S. Pat. No. 2,970,160, which is incorporated herein by reference.

The preferred betaine amphoteric surfactants include the alkylbetaines such as cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethylgamma-carboxypropylbetaine, lauryl-bis-(2-hydroxypropyl)-carboxyethylebetaine, and the like; the sultaines such as cocodimethylpropylsultaine, stearyldimethylpropylsultaine, lauryl-bis-(2-hydroxyethyl) propylsultaine and the like; and the amidosultaines such as cocoamidodimethylpropylsultaine, stearylamidodimethylpropylsultaine, laurylamidobis-(2-hydroxyethyl) propylsultaine, and the like.

The preferred phosphobetaines include lauric-myristicamido-3-hydroxypropylphosphobetaine, cocoamidodidsodium-3-hydroxypropylphosphobetaine, lauric-myristicamidodisodium-3-hydroxypropylphosphobetaine, lauric-myristicamidoglyceryl-phosphobetaine, lauric-myristicamidocarboxydisodium-3-hydroxypropylphosphobetaine, and the like. The preferred phosphitaines include cocoamidopropylmonosodiumphosphitaine, lauric-myristicamidopropylmonosodiumphosphitaine and the like.

The preferred n-alkylamino propionates and n-alkylimino dipropionates include those having the following structures:

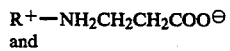
and

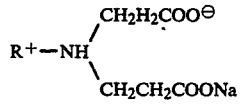

wherein R is from about 8 to 22 carbon atoms and mixtures thereof.

The amphoteric detergents may be present in an amount from about 2 to 10% by weight of the total composition.

It is envisioned that any anionic surfactant may be used in the compositions of the invention such as, for example, an alkyl sulfate of the formula R—CH$_2$—OSO$_3$X, an alkylether sulfate of the formula R(OCH$_2$CH$_2$)$_p$-alkylmonoglyceryl ether sulfonate of the formula

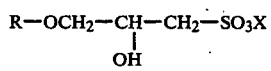

an alkylmonoglyceride sulfate of the formula

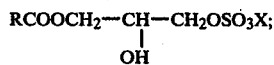

an alkylmonoglyceride sulfonate of the formula

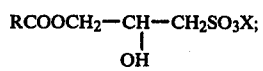

an alkyl sulfonate of the formula

and an alkylaryl sulfonate of the formula

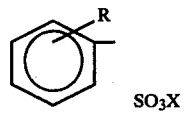

wherein
R is alkyl having from 7 to 17 carbon atoms;
X is selected from the group consisting of alkali metal ions, alkaline earth metal ions, ammonium ions, and ammonium ions substituted with from 1 to 3 lower alkyls and
p is an integer from 1 to 6.

The anionic detergent may be present in an amount of from about 2 to 10% by weight of the total composition.

Nonionic detergents which are useful include the alkylene oxide ethers of phenols, fatty alcohols, and alkyl mercaptans; the alkylene oxide esters of fatty acid amides; the condensation products of ethylene oxide with partial fatty acid esters, and mixtures thereof. The polyoxyalkylene chain in such agents may contain from 5 to 100 alkylene oxide units in which each alkylene unit has from 2 to 3 carbon atoms.

The nonionic surfactant may be present in an amount of from about 1 to 30% by weight of the total composition. Cationic surfactants suitable in these compositions include mono- and bis-quaternary ammonium halides, such as stearyldimethylbenzylammonium chloride, cetyltrimethylammonium chloride, N,N-dioctadecyl-N,N,N',N'-tetramethyl-1,5-(3-oxapentylene)diammonium bromide; tertiary amine salts such as cocoamidopropyldimethylamine hydrochloride stearylamidopropyldimethylamine citrate; cationic polymers such as hydroxyethyl cellulose reacted with epichlorohydrin and then quanternized with trimethylamine (Polymers of this type are sold by Union Carbide under the tradename Polymer JR) and specific triesters of phosphoric acid. The specific triesters of phosphoric acid are described in copending patent application Ser. No. 59,838 filed July 23, 1979, which is incorporated herein by reference. The cationic surfactants should be present in an amount of from about 0.5 to 3.0% by weight of the total composition.

The total amount of the active surfactant ingredients in the present invention should not be greater than about 50% by weight of the total composition in order to avoid ocular irritation problems, preferably from about 5 to 20% by weight of the total composition with the proviso that the total amount of anionic surfactant and amphoteric surfactant should not exceed 20% by weight of the total composition. In addition, other ingredients conventionally added to surfactant compositions for personal use, such as dyes, preservatives, perfumes, thickeners, opacifiers, conditioners, emollients, buffering agents, and the like, may be added in minor amounts. Ingredients such as dyes, preservatives and perfumes together usually constitute less than 2% by weight of the total composition and thickeners may be added to the composition in an amount of from about 1 to about 3% by weight of the total composition.

The detergent compositions of the present invention should have a pH in the range of about 6.5 to 8.5, preferably from about 7.0–7.5.

Liquid detergent compositions utilizing the complexes of the present invention can be prepared by admixing the amphoteric-alkoxylated carboxylate complex with the other surfactant(s) at room temperature or slightly elevated temperatures (about 50° C.) and then sufficient deionized water is added to bring the composition to about three quarters of its intended weight. Other ingredients such as various detergency adjuncts, fillers, carriers, perfumes, preservatives, gelling agents and the like are added as required followed by the balance of the water. The pH is then adjusted to within the desired range by the addition of strong acid, e.g., HCl, or strong base NaOH, as needed.

Detergent bar compositions utilizing the complexes of the present invention can be prepared by admixing the amphoteric—alkoxylated carboxylate complex with the other surfactant(s) in a stream jacketed rotary mixer at temperatures within the range of 60°–80° C. Fillers, whitening agents and processing oils can be added, as needed, to the hot slurry. After adequate mixing to assure homogeneity and moisture balance the product is chill rolled or drum dried into flakes. Dyes and fragrances are added to the flakes in a standard amalgamator together with additional water to provide proper bar formation. After adequate mixing the flakes are milled and plodded into logs which are then cut into blanks prior to stamping into bar form.

The detergent compositions of the present invention can be tested for ocular irritation by the following modified Draize Test (J. H. Draize et al., Toilet Goods Assn. No. 17 May 1952, No. 1, Proc. Sci. Sect.).

An 0.1 ml. sample of a neutral composition under test is dropped into one eye of an albino rabbit, the other eye serving as a control. Six rabbits are employed for each composition. Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, as the case may be.

Detergent compositions of the invention provide high foam volume and moreover outstanding foam stability as measured by an adaption of the well-known Ross-Miles foam test principle "Oil and Soap" 18.9–102 (1941):

Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45° C. in order to dissolve the lanolin in the dioxane. The remainder of the dioxane is then added and mixed. This lanolin dioxane solution, which is stored in an amber bottle, should be prepared fresh on the day that the tests were run.

The composition to be tested is diluted by adding 376 cc. of distilled water to 4 grams of the composition, and then by adding 20 cc. of the lanolin-dioxane solution described above while mixing. Heat is produced when the lanolin-dioxane solution is added to the solution of the composition in water and care must be taken in adjusting the temperatures of this solution to 24°–25° C. Both of these intermediate solutions should therefore be adjusted to 23° C. before mixing. The cooling of the lanolin-dioxane solution should be gradual in order to avoid precipitation of the lanolin. This will produce a final solution with a temperature of 24°–25° C.

The final solution of the composition to be tested, water, dioxane and lanolin described above, is then run in a modified Ross-Miles foam column in the usual way. All tests are conducted in duplicate, and the average of the two results is taken. Foam stability is determined by measuring the decay in foam height after two minutes, expressed as a percentage of the original height.

Specific embodiments of the present invention are illustrated by the following representative examples. It will be understood, however, that the invention is not confined to the specific limitations set forth in the individual examples, but rather to the scope of the appended claims.

EXAMPLE I 34.05 grams (0.05 g/moles) of a 24% active solution of an amphoteric of the formula

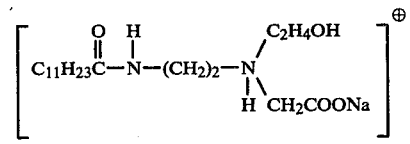

are mixed with 55.74 grams (0.075 g/moles) of a compound (75% active) of the formula:

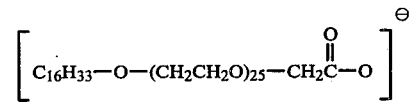

The pH is adjusted to 7.0 with a 10% NaOH solution.

The resulting product is a clear, semi viscous solution containing 25% actives solids with a pH of 7.1 and is an amphoteric-alkoxylated carboxylate complex of the structure shown as compound G in the specification. The complex is a slight ocular irritant when tested in accordance with the modified Draize Test procedure and provides good initial foam height when tested in the modified Ross-Miles foam column.

EXAMPLE II

The slurry obtained in Example I is freeze-dried by known procedures to yield about 95% solids. The solids are ground to a slightly tacky powder which can be utilized to form a bar soap.

EXAMPLE III

Following the procedures of Example I, the amphoteric of Example I is mixed with a compound of the following formula $C_{13}H_{27}+O-CH_2-CH_2\text{-})_6O-CH_2COO^\ominus$ to form the amphoteric-alkoxylated carboxylate complex shown as compound A in the specification.

EXAMPLE IV

Following the procedures of Example I, 227 grams (0.15 g/moles) of a 22% active solution of tetradecyliminodicarboxylate are dissolved in 450 grams of deionized water at a temperature of about 50°-60° C. 118.2 grams (0.15 g/moles) of a compound of the formula

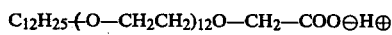

is added to form compound B as shown in the specification. This complex foams copiously when tested according to the modified Ross-Miles procedure.

EXAMPLE V 300 grams (0.07 g./moles) of an 11.1% active solution of an amphoteric of the formula

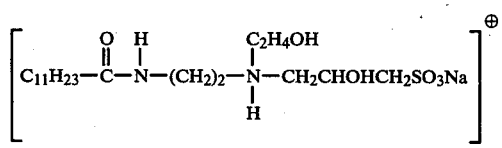

are mixed with 105.6 grams (0.07 g/moles) of a compound of the formula

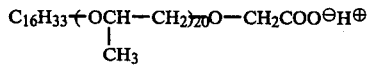

to form an amphoteric-alkoxylated carboxylate of the following structure:

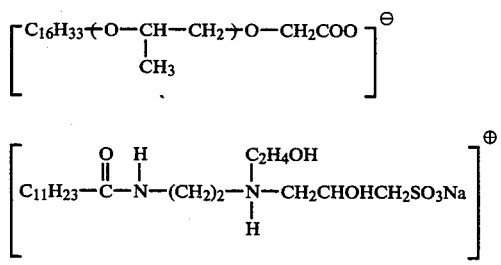

EXAMPLE VI 360 grams (0.19 g./moles) of a 19.1% active solution of an amphoteric of the formula

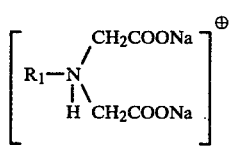

wherein $R_1$ has an alkyl chain length percent distribution as follows: $C_{10}$-2, $C_{12}$-53, $C_{14}$-24, $C_{16}$-11 $C_{18}$-10; are mixed with 286.6 grams (—0.19 g/moles) of a compound of the formula

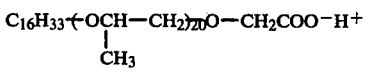

to form an amphoteric-alkoxylated carboxylate of the formula:

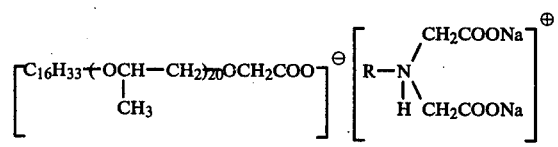

EXAMPLE VII

A clear gel hair care product is prepared as follows: 200 grams of deionized water are charged to a vessel equipped with an agitator and steam. 150 grams of Compound A are added and the solution is mixed until clear. 20 grams of polyethylene glycol 6000 distearate are added and heat is applied to the solution to 70° C. for twenty minutes. The solution is cooled to 25°-30° C. and 1.0 grams of preservative, 2.0 grams of fragrance and sufficient deionized water is added to bring the total weight to 1000 grams.

The resulting product has the following compositions:

|  | wt./wt. % |
| --- | --- |
| Compound A | 15.00 |
| polyethylene glycol 6000 distearate | 2.00 |
| preservative | 0.10 |
| fragrance | 0.20 |
| deionized water | q.s. to 100% |

EXAMPLE VIII

An opaque liquid soap is prepared having the following formulation:

|  | wt./wt. % |
| --- | --- |
| Compound A | 15.00 |
| Compound C | 15.00 |
| Cabosil (tradename for colloidal silica, available from Cabot Corp., Boston, Mass.) | 3.50 |
| isopropanol | 0.10 |
| fragrance | 0.30 |
| deionized water | q.s. to 100% |

The pH of the above formulation is adjusted to 6.5 with citric acid.

EXAMPLE IX

A clear, liquid hair cleanser composition is prepared having the following formulation:

|  | wt./wt. % |
| --- | --- |
| Compound A | 5.00 |
| polyoxyethylene 80 sorbitan monolaurate | 10.00 |
| Deriphat (tradename for salt of N—alkyl beta-iminopropionic acid available from General Mills Inc., Kankekee, Illinois) | 5.00 |
| polyethylene glycol 6000 distearate | 2.00 |

-continued

| | wt./wt. % |
|---|---|
| benzyl alcohol | 0.10 |
| Dowicil 200 (tradename for the cis isomer of 1-(3-chloroalkyl)-3,5,7-triaza-1-azoniaadamantine chloride) | 0.10 |
| fragrance | 0.20 |
| deionized water | q.s. to 100% |

The above formulation is adjusted to a pH of 7.1 with 15% HCl and has a viscosity of 413 cps. at 25° C. and is a slight ocular irritant. The formulation also exhibits good foam properties.

EXAMPLE X

A detergent bar composition is prepared as follows: 20 parts of Compound E are mixed with 50 parts of sodium lauryl sulfate/sulfo succinate (1:1 weight ratio). After the slurry is homogeneous, 9 parts of stearic acid are added followed by the addition of 9 parts each of talc and dextrin. The batch is mixed 20 minutes, cooled, milled into ribbons and pressed into detergent bars.

The resulting bars have the following formulation:

| | wt./wt. % |
|---|---|
| Compound E | 20.00 |
| sodium lauryl sulfate | 25.00 |
| sulfosuccinate | 25.00 |
| stearic acid | 9.00 |
| talc | 9.00 |
| dextrin | 9.00 |
| water | q.s. to 100.00 | and has a pH of 7.0. This product is a moderate irritant and exhibits excellent foaming properties.

In addition to the preferred embodiments described herein, other embodiments, arrangements and variations within the spirit of the invention and the scope of the appended claim will occur to those skilled in the art.

What is claimed is:

1. A complex of the formula

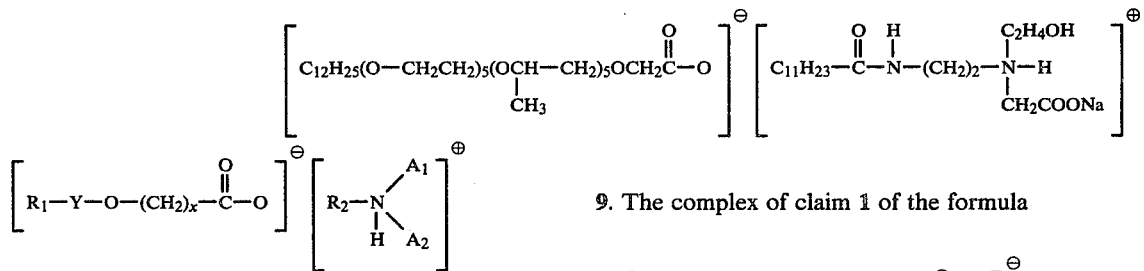

wherein
$R_1$ is alkyl or substituted alkyl containing from about 6 to 18 carbon atoms and mixtures thereof;

$R_2$ is alkyl containing from about 8 to 18 carbon atoms and mixtures thereof or alkyl amido of the formula

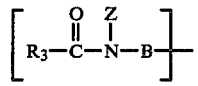

wherein
$R_3$ is alkyl containing from about 7 to 17 carbon atoms;
Z is H or lower alkyl containing from 1 to 4 carbon atoms; and
B is lower alkyl containing from 1 to 4 carbon atoms;
x is an integer from 1 to 3;
$A_1$ and $A_2$ are the same or different and are selected from the group of anionic salt moieties consisting of the following:

$-[CH_2CH_2-COOX]_n$ $-[CH_2-COOX]_n$ $-[CH_2CHOH-CH_2-SO_3X]_n$ $-[CH_2-CHOH-CH_2-OPO_3X]_n$ wherein X is a water soluble cation and n is an integer of 1 or 2 with the proviso that if only one of $A_1$ and $A_2$ are selected from the anionic salt moieties above, the other can be lower alkyl or lower hydroxyalkyl containing from 1 to 4 carbon atoms;

and wherein the pH of the complex is in the range from about 6.5 to 8.5 and wherein the ratio of alkoxylated carboxylate to amphoteric is within the range of from 0.5:1 to 1.5:1.

2. The complex of claim 1 wherein $R_1$ is $C_{12}H_{25}$.
3. The complex of claim 1 wherein $R_2$ is $C_{14}H_{29}$.
4. The complex of claim 1 wherein $R_2$ is $C_{12}H_{25}$.
5. The complex of claim 1 wherein $R_1$ is $C_{16}H_{33}$.
6. The complex of claim 1 wherein $A_1$ and $A_2$ are $(CH_2COOX)_n$.
7. The complex of claim 1 of the formula

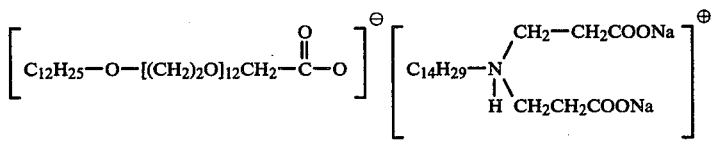

8. The complex of claim 1 of the formula

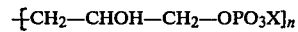

9. The complex of claim 1 of the formula

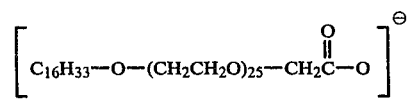

-continued
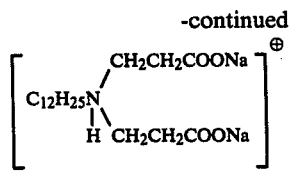
10. A detergent composition wherein the active ingredients comprise from about 1 to 50% by weight of the total composition of at least one complex of the formula of claim 1.
* * * * *

UNITED STATES PATENT AND TRADEMARK OFFICE
CERTIFICATE OF CORRECTION

PATENT NO. : 4,443,362
DATED : April 17, 1984
INVENTOR(S) : Guth et al.

It is certified that error appears in the above-identified patent and that said Letters Patent is hereby corrected as shown below:

Column 12, Claim 1, line 15, after ". . . 1 to 3;"
add on the following line:

-- Y is $\{O-CH_2-CH_2\}_a$, $\{O-CH(CH_3)-CH_2\}_b$ or mixtures thereof wherein a and b are the same or different and are integers of from 1 to 100; --

Signed and Sealed this

Second Day of December, 1986

Attest:

DONALD J. QUIGG

Attesting Officer

Commissioner of Patents and Trademarks